(12) United States Patent
Stock et al.

(10) Patent No.: US 10,460,121 B2
(45) Date of Patent: Oct. 29, 2019

(54) ELECTRONIC AUTHORIZATION DEVICE

(71) Applicant: Robert Bosch GmbH, Stuttgart (DE)

(72) Inventors: Joern Stock, Wernau (DE); Florian Esenwein, Leinfelden-Echterdingen (DE); Joachim Schadow, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 270 days.

(21) Appl. No.: 15/383,152

(22) Filed: Dec. 19, 2016

(65) Prior Publication Data
US 2017/0177894 A1 Jun. 22, 2017

(30) Foreign Application Priority Data

Dec. 21, 2015 (DE) .......................... 10 2015 226 198

(51) Int. Cl.
| | | |
|---|---|---|
| *G06F 21/62* | (2013.01) | |
| *A61B 5/00* | (2006.01) | |
| *A61B 5/117* | (2016.01) | |

(52) U.S. Cl.
CPC ........ *G06F 21/6218* (2013.01); *A61B 5/0002* (2013.01); *A61B 5/117* (2013.01)

(58) Field of Classification Search
CPC .................................................. G06F 21/6218
USPC ......................................................... 340/5.82
See application file for complete search history.

(56) References Cited

U.S. PATENT DOCUMENTS

| | | | | |
|---|---|---|---|---|
| 5,205,436 A | * | 4/1993 | Savage | ..................... A47F 3/02 221/1 |
| 6,840,451 B2 | * | 1/2005 | Allen | ..................... G06Q 10/06 235/462.09 |
| 7,928,845 B1 | * | 4/2011 | LaRosa | .............. G08B 13/1427 340/539.21 |
| 8,020,768 B2 | * | 9/2011 | Ramos-Elizondo | ........................ G06Q 10/087 235/385 |
| 8,842,183 B2 | * | 9/2014 | Glickman | ................ G06K 9/00 348/165 |
| 9,122,999 B2 | * | 9/2015 | Jackson | ............... G06Q 10/087 |
| 9,147,174 B2 | * | 9/2015 | Glickman | .............. G06K 9/209 |
| 9,412,124 B2 | * | 8/2016 | Bonner | ................ G07G 1/0045 |
| 9,811,962 B2 | * | 11/2017 | Phillips | .............. G06K 9/00771 |
| 9,864,971 B2 | * | 1/2018 | Daily | ...................... A47F 9/047 |
| 10,013,834 B2 | * | 7/2018 | Phillips | .............. G06K 9/00771 |
| 10,062,050 B2 | * | 8/2018 | Lipsey | ..................... G06K 9/00 |
| 2003/0051075 A1 | * | 3/2003 | Purpura | .................. H04L 41/00 710/1 |
| 2005/0110638 A1 | * | 5/2005 | Mohr | ................... G06Q 10/087 340/572.1 |
| 2005/0128083 A1 | * | 6/2005 | Puzio | ..................... G08B 13/14 340/572.1 |
| 2018/0211345 A1 | * | 7/2018 | Bean | ....................... G01S 11/06 |

* cited by examiner

*Primary Examiner* — Santiago Garcia
(74) *Attorney, Agent, or Firm* — Maginot, Moore & Beck LLP

(57) ABSTRACT

A method is proposed for authorizing use of at least one object, in particular at least one machine, in particular at least one hand-held power tool, in which at least one evaluation unit of an electronic authorization device provides an item of authorization information at least in dependence on at least one item of use-related information.

17 Claims, 9 Drawing Sheets

ELECTRONIC AUTHORIZATION DEVICE

This application claims priority under 35 U.S.C. § 119 to application no. DE 10 2015 226 198.0, filed on Dec. 21, 2015 in Germany, the disclosure of which is incorporated herein by reference in its entirety.

BACKGROUND

A method for authorizing use of at least one object, in particular at least one machine, in particular at least one hand-held power tool, has already been proposed.

SUMMARY

A method is proposed for authorizing use of at least one object, in particular at least one machine, in particular at least one hand-held power tool, in which at least one evaluation unit of an electronic authorization device provides an item of authorization information, at least in dependence on at least one item of use-related information.

This allows particularly flexible authorization to be achieved. Unauthorized use of the object, in particular the machine, in particular the hand-held power tool, can be conveniently and reliably avoided. A high degree of work safety can be achieved.

An "object" is intended to be understood in this connection as meaning in particular a technical device, for example a vehicle, in particular a motor vehicle, or an implement, such as for example a machine, a hand-held power tool, a garden implement, a measuring instrument, a ladder or a container, such as for example a machine case or a material cupboard. A "hand-held power tool" is intended to be understood as meaning in particular a workpiece-machining tool, advantageously however a power drill, a hammer drill and/or percussion hammer, a saw, a plane, a screwdriver, a milling cutter, a grinder, an angle grinder, a garden implement and/or a multifunctional tool. An "evaluation unit" is intended to be understood as meaning in particular a unit with an information input, information processing and an information output. The evaluation unit advantageously has at least one processor, a memory, input and output means, other electrical components, an operating program, closed-loop control routines, open-loop control routines and/or calculation routines. The components of the computing unit are preferably arranged on a common printed circuit board and/or advantageously in a common housing. An item of "use-related information" is intended to be understood in this connection as meaning in particular an item of information relating to a work order, relating to a user, relating to an infrastructure unit, for example a gate or an area or a room, and/or relating to personal protective equipment. An item of information "relating" to an article or a person is intended to be understood in this connection as meaning in particular an item of information that identifies the article or the person more specifically, comprises at least one characteristic of the article or the person and/or quantifies a descriptive variable of the article and/or the person. It is conceivable that the authorization information is formed as a bivalent item of information, which enables or disables use of the at least one object by the user. It is conceivable that the authorization information is complex and is formed for example as a keycode or is determined on the basis of a keycode, which preferably comprises a daily-updated part and a further part relating to a user. The further part comprises for example assessments and/or values of a loading variable, such as for example an amount of vibration, an amount of noise, a radiation exposure, a stress level, and/or an accumulated working time. For example, for determining an item of authorization information, the evaluation unit classifies a value of the loading variable.

In an advantageous way, in at least one method step, the at least one evaluation unit provides the authorization information at least in dependence on at least one item of information relating to a user. This allows an individualized authorization to be achieved. Work safety can be further increased. An item of information "relating to a user" is intended to be understood in this connection as meaning in particular an identity, an age, a level of training, a person's physical condition or a loading variable, such as for example an amount of vibration, an amount of noise, a radiation exposure, loading as a result of high and/or low temperatures, a stress level and/or an accumulated working time and/or any further loading as a result of environmental influences that appears suitable to a person skilled in the art.

It is also proposed that, in at least one method step, the at least one evaluation unit is fastened to an extremity of the user by means of a fastening unit of the authorization device. This allows a particularly conveniently usable authorization device to be provided. A high level of acceptance of the authorization device can be achieved. A closed state of the fastening device may be advantageously used for an authorizing operation, for example as a start signal for the authorizing operation. The fastening unit preferably has at least one arm band and/or ankle band, an adhesive element, a hook-and-loop element and/or some other connecting element that appears suitable to a person skilled in the art.

It is also proposed that, in at least one method step, the at least one evaluation unit reads in, erases, activates and/or deactivates authorization data in dependence on a state and/or in dependence on a change in state of the fastening unit. This allows a large number of authorization data to be used. A particularly efficient process for using authorization data can be achieved. A "change in state" of the fastening unit is intended to be understood in this connection as meaning in particular a transition from a closed state into an open state or from an open state into a closed state. It is conceivable that the evaluation unit reads in, erases, activates and/or deactivates authorization data in dependence on a user input. For example, in a fixed time interval after the closing of the fastening unit, the evaluation unit expects the user to identify himself or herself, and/or it reads in authorization data, such as for example qualifications of the user, data on a work order and/or clearances for certain job sites, for example areas of a building. It is conceivable that the data are read in in a multistage process. For example, data on a work order include details of a working area, and, in a subsequent step, the evaluation unit reads in authorization data for the working area.

It is also proposed that, in at least one method step, at least one sensor unit of the authorization device senses data, in particular individual body data, of the user for an identification of the user and transmits the data to the at least one evaluation unit. This allows a user to be identified particularly reliably, conveniently and/or efficiently. In particular, the at least one sensor unit is connected in signaling terms to the evaluation unit. The fastening unit preferably has a housing, in which the at least one sensor unit is arranged. It is conceivable that the at least one sensor unit is arranged on an item of personal protective equipment. For example, the at least one sensor unit has an optical skin scanning unit, an infrared skin scanning unit, a body odor sensor, a DNA analysis unit and/or a face recognition unit. In particular, the evaluation unit provides the authorization information at least in dependence on the value sensed by the sensor unit.

It is also proposed that, in at least one method step, the at least one sensor unit of the authorization device senses a value of at least one loading variable acting on the user and/or a value of a capability parameter of the user and transmits the data to the at least one evaluation unit. This allows working conditions and/or the capability of the user to be sensed particularly reliably. In particular, the sensor unit is connected in signaling terms to the evaluation unit. The "capability parameter" is intended to be understood in this connection as meaning for example a strength, a time-dependently sensed movement pattern, a responsiveness and/or a parameter that describes a person's physical condition, such as for example a blood pressure, a pulse rate, a body temperature. In particular, the evaluation unit provides the authorization information at least in dependence on the value sensed by the sensor unit.

In an advantageous way, in at least one method step, the at least one evaluation unit provides the authorization information at least in dependence on the level of training of the user, in dependence on a value of at least one loading variable acting on the user and/or in dependence on a value of at least one capability parameter of the user. This allows a work-related load on the user to be effectively limited. An ability to work can be maintained. A "level of training" is intended to be understood in this connection as meaning in particular data on education, vocational training, courses of instruction and/or training sessions. The evaluation unit advantageously compares the value of at least one loading variable acting on the user with a threshold value for the loading variable. The evaluation unit preferably compares the value of the at least one capability parameter with a threshold value for the capability parameter.

In an advantageous way, in at least one method step, the at least one evaluation unit provides the authorization information at least in dependence on at least one item of information relating to at least one spatial working area. This allows a comprehensive safety concept to be put into practice. A "spatial working area" is intended to be understood in this connection as meaning in particular a room of a building or a space in a vehicle, a zone in a room of a building or in a space in a vehicle, an area outdoors or a combination of these areas. The spatial working area is preferably assigned to at least one infrastructure unit, such as an access control unit, for example a gate or a door.

It is also proposed that, in at least one method step, the at least one evaluation unit provides the authorization information at least in dependence on an access authorization of a user to the spatial working area and/or in dependence on a permission to use the at least one object in the spatial working area. This allows a specifically adapted safety concept to be put into practice. The access authorization and/or the permission to use something is/are preferably dependent on an assessment of the potential danger of the spatial working area. It is conceivable that the access authorization and/or the permission to use something is/are dependent on a prior use and/or a contamination of the spatial working area. It is conceivable that the access authorization is dependent on a physical constitution of the user, for example a sensitivity and/or allergy. It is conceivable that the access authorization is dependent on a confidentiality status.

In an advantageous way, in at least one method step, the at least one evaluation unit actively adapts the authorization information to a changed access authorization of the user in relation to the spatial working area and/or to a changed permission to use the at least one object in the spatial working area. This allows a particularly flexible safety concept to be achieved. Particularly efficient working processes can be achieved. The evaluation unit preferably adapts the authorization information repeatedly, preferably regularly, particularly preferably periodically, to the changed access authorization of the user in relation to the spatial working area and/or to the changed permission to use the at least one object in the spatial working area. The evaluation unit preferably requests the data on the changed access authorization of the user in relation to the spatial working area and/or in relation to the changed permission to use the at least one object in the spatial working area repeatedly, preferably regularly, particularly preferably periodically.

It is also proposed that, in at least one method step, the at least one evaluation unit exchanges data with at least one infrastructure unit. This allows a particularly efficient and/or reliable data exchange to be achieved. A decentralized and/or redundant data exchange can be achieved. An "infrastructure unit" is intended to be understood in this connection as meaning in particular a transmitting unit assigned to a spatial working area and/or an access control unit that has for example a turnstile, a barrier and/or a door. The evaluation unit preferably exchanges data with the at least one infrastructure unit repeatedly, preferably regularly, particularly preferably periodically.

In an advantageous way, in at least one method step, the at least one evaluation unit provides the authorization information at least in dependence on at least one item of information relating to an item of personal protective equipment. In this way, a comprehensive safety concept can be put into practice. The personal safety equipment preferably comprises at least one item of protective clothing, goggles, a helmet, ear defenders, gloves, a respirator unit, shoes and/or further elements that appear appropriate to a person skilled in the art. For example, the information relating to the personal protective equipment comprises an item of information concerning its condition, age, completeness, information concerning a connection of elements of the protective equipment and/or any further information that appears appropriate to a person skilled in the art.

It is also proposed that, in at least one method step, the at least one evaluation unit provides the authorization information in dependence on a necessity for the personal protective equipment for using the at least one object and/or in dependence on a necessity for the personal protective equipment for at least one spatial working area. As a result, safety-relevant information can be linked together in a particularly advantageous way. The necessity for personal protective equipment for using the at least one object is preferably dependent on an assessment of the potential danger of the at least one object. In particular, the necessity for the personal protective equipment for the at least one spatial working area is dependent on an assessment of the potential danger of the at least one spatial working area.

In an advantageous way, in at least one method step, the at least one evaluation unit actively adapts the authorization information to a changed necessity for the personal protective equipment for the at least one spatial working area. This allows a flexibility of a safety concept to be further increased. The evaluation unit preferably adapts the authorization information repeatedly, preferably regularly, particularly preferably periodically, to a changed necessity for the personal protective equipment for the at least one spatial working area. The evaluation unit preferably requests data on the changed necessity for the personal protective equipment for the at least one spatial working area repeatedly, preferably regularly, particularly preferably periodically.

It is also proposed that, in at least one method step, at least one wear sensor unit of the authorization device senses at least one value for determining a state of wear of the personal protective equipment and transmits it to the at least one evaluation unit. This allows a risk of potential danger to be avoided particularly effectively. For example, the wear sensor unit is intended to sense an absence of elements, aging, fragility, damage and/or malfunctioning.

In an advantageous way, in at least one method step, at least one scanning unit of the authorization device senses an arrangement of the personal protective equipment. This allows an arrangement of the personal protective equipment to be sensed in a way that is particularly convenient for a user. The scanning unit is preferably arranged on the fastening unit for the evaluation unit. In an alternative configuration, the scanning unit is arranged on an infrastructure unit. In particular, the scanning unit is connected in signaling terms to the evaluation unit. A "scanning unit" is intended to be understood in this connection as meaning in particular an optical and/or a radio scanning unit, which is for example intended to sense markings, in particular optical markings, and/or RFID tags, which are arranged on elements of the protective equipment. The scanning unit preferably comprises a camera.

It is also proposed that, in at least one method step, the at least one sensor unit senses a state of use of the personal protective equipment and/or a movement carried out with the personal protective equipment and transmits it to the at least one evaluation unit. This advantageously allows preparation for work to be used for checking the personal protective equipment. For example, the sensor unit senses an operation in which the personal protective equipment is put on. The sensor unit is preferably arranged on the personal protective equipment and senses directly whether the personal protective equipment is being worn, and comprises for example at least one contact sensor, a heat sensor, an acceleration sensor and/or some other sensor that appears appropriate to a person skilled in the art. In particular, the sensor unit is intended for wireless communication with the evaluation unit.

In an advantageous way, in at least one method step, the at least one evaluation unit evaluates the movement carried out with the personal protective equipment. This allows a state of use of the personal protective equipment to be checked continuously and/or particularly reliably. The evaluation unit is preferably intended for a comparison of movements carried out with the personal protective equipment with movement patterns stored in the evaluation unit and/or in a database.

It is also proposed that, in at least one method step, the at least one evaluation unit wirelessly exchanges data with the at least one object. This allows a high degree of user convenience to be achieved. An authorization device that can be used particularly diversely can be provided. In particular, in at least one method step, the evaluation unit transmits the authorization information to the object. The evaluation unit preferably has an interface with a wireless data transmission according to a data transmission standard, such as for example Bluetooth, BLE, RFID, Wi-Fi, ZigBee, NFT or according to some other standard that appears appropriate to a person skilled in the art.

In an advantageous way, in at least one method step, the at least one evaluation unit wirelessly exchanges data with at least one further object. This allows a method that can be used particularly flexibly to be achieved. In particular, the evaluation unit exchanges an item of authorization information for the at least one further object with the object. It is conceivable that the evaluation unit evaluates the authorization information for the object and for the at least one further object in mutual dependence.

It is also proposed that, in at least one method step, the at least one evaluation unit exchanges data with at least one authorization database. This allows particularly reliable management of authorization data to be achieved. Data consistency can be achieved in an easy way. An "authorization database" is intended to be understood in this connection as meaning in particular a database with authorization data, such as for example data on the level of training of the user, data on an assignment of the object and/or of the user to a use and/or to a work order, data on a necessity for personal protective equipment relating to the object and/or a spatial working area, data on use of an area or a room, access authorizations for areas of a building and/or of a site, data on a necessity for personal protective equipment relating to a use, to a work order and/or to the at least one object, data on movement patterns for a comparison with sensed data. It is conceivable that the evaluation unit and the authorization database exchange data via a network and/or via a cloud.

It is proposed that the at least one external evaluation unit advantageously evaluates data on providing the authorization information and transmits at least one evaluation result to the at least one evaluation unit. In this way, resources for a complex evaluating operation can be provided. The external evaluation unit can evaluate authorization data redundantly with respect to the evaluation unit. A particularly reliable evaluation can be achieved. In particular, the at least one external evaluation unit and the at least one evaluation unit are functionally connected to one another. For example, the at least one external evaluation unit is formed as part of a cell phone or as part of a portable computer device, such as a tablet or a laptop. It is conceivable that the at least one external evaluation unit is formed as part of a stationary computer device.

It is also proposed that, in at least one method step, the at least one evaluation unit transmits an item of information, in particular the authorization information, for an output to a user to at least one output unit. This allows a working process to be controlled particularly easily. An absent authorization can be detected at an early time. The at least one output unit is preferably arranged in a housing of the fastening unit. It is conceivable that the at least one output unit is formed as an external output unit, such as for example as a display of a cell phone. The output unit preferably has a display. It is conceivable that the output unit alternatively or additionally comprises visual, acoustic and/or haptic output elements.

In an advantageous way, in at least one method step, the at least one evaluation unit receives input data from at least one input unit. This advantageously allows a man-machine communication to be achieved. The at least one input unit is preferably arranged in a housing of the fastening unit. The at least one input unit preferably has at least one key element and/or a keypad. It is conceivable that the at least one input unit is formed as at least partially integrated with an output unit, for example as a touchscreen. It is conceivable that the at least one input unit is formed as an external input unit.

An electronic authorization device is also proposed, in particular for carrying out a method according to the disclosure, with at least one evaluation unit, for authorizing use of at least one object, in particular at least one machine, in particular at least one hand-held power tool, and in particular with at least one fastening unit for fastening to an extremity of a user, the at least one evaluation unit being intended for providing an item of authorization information at least in dependence on at least one item of use-related information. In this way, an authorization unit that is particularly reliable and/or can be used particularly flexibly can be provided. Particularly safe operation of the object, in particular the hand-held power tool, can be achieved.

An object system is also proposed, with at least one object, in particular a machine, in particular a hand-held power tool, and with at least one electronic authorization device according to the disclosure. In this way, unauthorized use of the object system can be avoided. An object system that can be operated particularly safely can be provided. The object system preferably comprises at least one further object.

The method according to the disclosure, the electronic authorization device and/or the object system is/are not intended here to be restricted to the use and embodiment described above. In particular, to function in the way described here, the method according to the disclosure, the electronic authorization device and/or the object system may have a number of individual elements, components and units and a number of method steps other than the number mentioned herein. Moreover, in the case of the ranges of values specified in this disclosure, values lying within the stated limits are also to be considered as disclosed and usable in any way desired.

BRIEF DESCRIPTION OF THE DRAWINGS

Further advantages emerge from the following description of the drawing. In the drawing, three exemplary embodiments of the disclosure are represented. The drawings and the description contain numerous features in combination. A person skilled in the art will also expediently consider the features individually and put them together into appropriate further combinations.

In the drawings.

DETAILED DESCRIPTION

Figure 1:
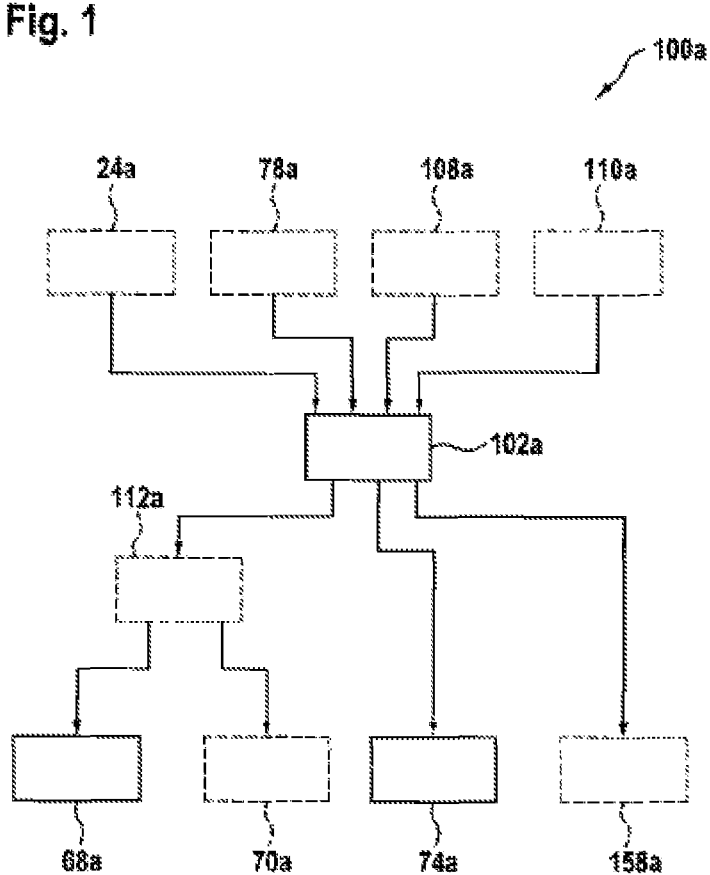
FIG. 1 shows a flow diagram of a method according to the disclosure for authorizing use of an object.

FIG. 1 shows a flow diagram 100a of a method for authorizing use of an object 10a. In the flow diagram 100a, method steps that may be omitted are shown by dashed lines. In the present exemplary embodiment, the object 10a is formed as a hand-held power tool. In the present exemplary embodiment, the object 10a is formed as an angle grinder (cf. FIG. 9). In the method, an evaluation unit 16a of an electronic authorization device 20a provides an item of authorization information at least in dependence on at least one item of use-related information. The use-related information relates for example to a work order, to a user, to an item of personal protective equipment 52a, and/or to a working area, such as for example to a building, to an area of a building, an area or a room and/or part of a site. The authorization information indicates whether the object 10a may be used for a use assessed by the authorization device 20a. In at least one evaluation step 102a, the evaluation unit 16a evaluates at least one item of use-related information and from it determines the authorization information. The authorization information is used for enabling or disabling the object 10a.

Figure 2:
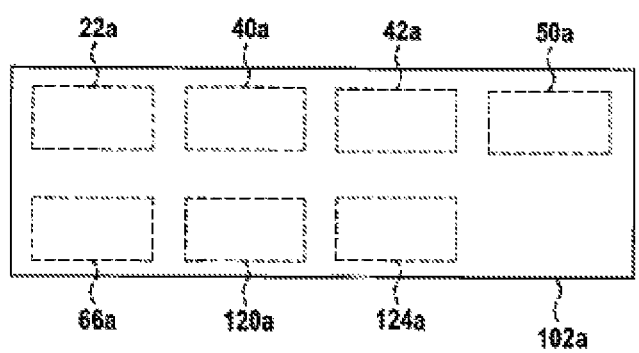
FIG. 2 shows an evaluation step of the method with possible substeps.

In one scenario, the use-related information comprises an item of user-related information. In at least one method step 22a, the evaluation unit 16a provides the authorization information in dependence on an item of information relating to the user. The method step 22a forms the evaluation step 102a or the evaluation unit 16a performs the method step 22a as a substep of the evaluation step 102a (cf. FIG. 2). The evaluation unit 16a evaluates information relating to the user and from it determines the authorization information. The authorization information indicates whether the object 10a may be used by the user for the use assessed by the authorization device 20a.

Figure 7:
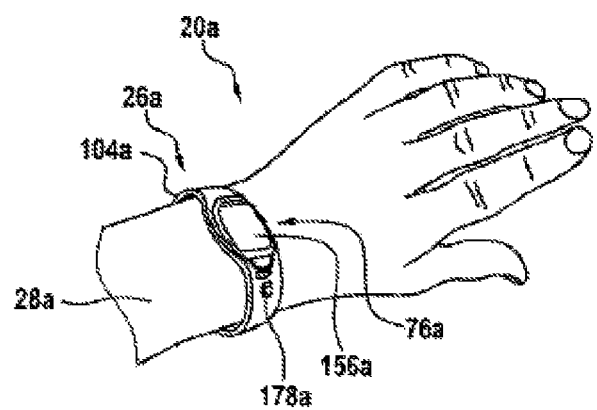
FIG. 7 shows a view of an extremity of a user to which the authorization device is fastened.

In at least one method step 24a, the evaluation unit 16a is fastened to an extremity 28a of the user by means of the fastening unit 26a of the authorization device 20a (cf. FIG. 7). In the present exemplary embodiment, the fastening unit 26a has an arm band 104a. In a closing operation, two open ends of the arm band 104a are connected to one another. For example, in a closing operation, a closure element 106a connects the two open ends of the arm band 104a. The openings are releasably connected to one another. It is also conceivable that the arm band 104a consists of a closed ring of a flexibly extensible material. To put it on, the arm band 104a is then slipped over the extremity 28a. In a closed state, the arm band 104a encloses the extremity 28a, for example an arm, of the user and the fastening unit 26a holds the evaluation unit 16a on the extremity 28a.

Figure 3:
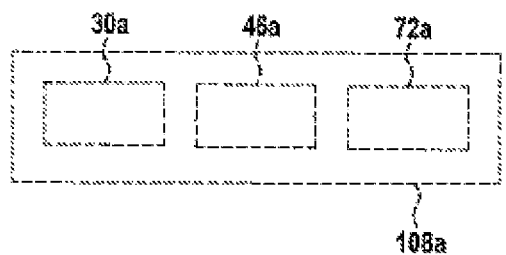
FIG. 3 shows a data exchange step of the method with possible substeps.

In at least one method step 30a, the evaluation unit 16a reads in authorization data in dependence on a state and/or in dependence on a change in state of the fastening unit 26a. It is conceivable that, in the method step 30a, the evaluation unit 16a stores authorization data, erases authorization data, for example authorization data of a previous work order, and/or activates or deactivates authorization data, for example authorization data stored in the evaluation unit 16a. The method step 30a forms a data exchange step 108a or the data exchange step 108a has the method step 30a as a substep (cf. FIG. 3). It is conceivable that the method step 30a is omitted. In the present exemplary embodiment, the evaluation unit 16a reads in use-related authorization data in a closed state of the fastening unit 26a. The authorization data indicate for example whether the object 10a is enabled for the work order at a given point in time. The authorization data comprise data relating to the work order, data relating to the user, access authorizations, permissions to use the object 10a and also threshold values, for example for loading variables and/or desired variables acting on the user. In the present exemplary embodiment, the evaluation unit 16a reads in authorization data relating to the user in a closed state and/or put-on state of the fastening unit 26a. It is conceivable that the evaluation unit 16a reads, erases, activates and/or deactivates the authorization data during putting on, closing, opening and/or taking off of the fastening unit 26a.

The authorization data relating to the user indicate for example whether the object 10a is enabled for the user at a current point in time and/or whether the user has received training and/or instruction required for a use of the object 10a and/or for the work order and/or whether the user has kept to required rest times. The evaluation unit 16a evaluates the received authorization data and checks for example whether it has been assigned to a user who has received training required for the use of the object 10a. In the present scenario, in at least one method step 40a, the evaluation unit 16a determines the authorization information at least in dependence on a level of training of the user. The method step 40a forms the evaluation step 102a or the evaluation unit 16a performs the method step 40a as a substep of the evaluation step 102a.

Figure 4:
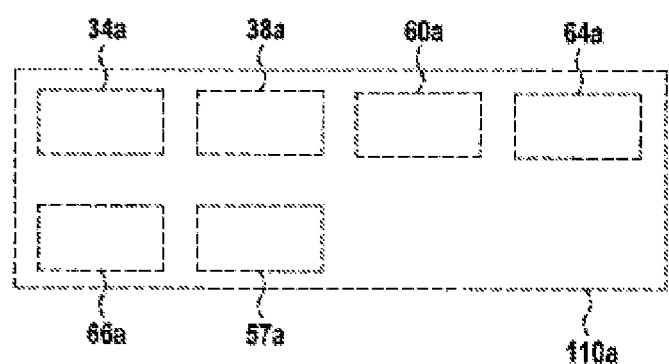
FIG. 4 shows a data sensing step of the method with possible substeps.
Figure 5:
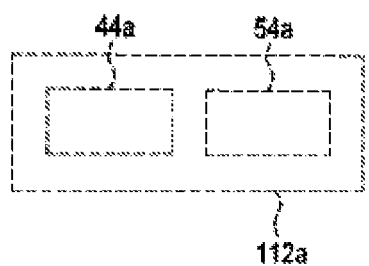
FIG. 5 shows an adaptation step of the method with possible substeps.

In one scenario, in at least one method step 34a, at least one sensor unit 32a senses data, in particular individual body data, of the user for an identification of the user and transmits the data to the evaluation unit 16a. The method step 34a forms a data sensing step 110a or the data sensing step 110a has the method step 34a as a substep (cf. FIG. 4). It is conceivable that the method step 34a is omitted. In the present exemplary embodiment, the sensor unit 32a has at least one skin sensor, which in at least one operating state senses a temperature, a moistness and/or a surface structure of the skin of the user. It is conceivable that the sensor unit 32a alternatively or additionally has at least one body odor sensor, which in at least one operating state senses odors given off by the skin of the user. It is conceivable that the sensor unit 32a alternatively or additionally has further sensors deemed appropriate by a person skilled in the art, for example a camera for face recognition and/or sensors for sensing data for a DNA analysis.

The evaluation unit 16a receives data sensed by the sensor unit 32a for sensing user data and evaluates them. The evaluation unit 16a identifies the user by means of the data sensed by the sensor unit 32a, for example the evaluation unit 16a compares the data sensed by the sensor unit 32a with data stored in the evaluation unit 16a and/or with data read in. In the present scenario, in the at least one method step 40a, the evaluation unit 16a determines the authorization information in dependence on the identification of the user. The method step 40a forms the evaluation step 102a or the evaluation unit 16a performs the method step 40a as a substep of the evaluation step 102a.

In one scenario, in at least one method step 38a, at least one sensor unit 36a senses loading data of the user and transmits the data to the evaluation unit 16a. The method step 38a forms the data sensing step 110a or the data sensing step 110a comprises the method step 38a as a substep. It is conceivable that the method step 38a is omitted.

The evaluation unit 16a receives data sensed by the sensor unit 36a for sensing loading data and evaluates them. The evaluation unit 16a accumulates the data provided by the sensor unit 36a and determines an overall loading. It is conceivable that the evaluation unit 16a alternatively or additionally determines a peak loading of the user. The evaluation unit 16a compares a current loading, an accumulated loading and/or a peak loading with stored and/or read-in limit values and from this determines the authorization information. In the present scenario, in the at least one method step 40a, the evaluation unit 16a provides the authorization information at least in dependence on a value of at least one loading variable acting on the user. The method step 40a forms the evaluation step 102a or the evaluation unit 16a performs the method step 40a as a substep of the evaluation step 102a.

In one scenario, in the at least one method step 38a, the sensor unit 36a senses a capability of the user and transmits the data to the evaluation unit 16a. The evaluation unit 16a receives data sensed by the sensor unit 36a on a capability of the user and evaluates them. The evaluation unit 16a compares movement patterns sensed by the sensor unit 36a with stored movement patterns and/or analyzes a speed and/or precision in the movements and determines a capability parameter of the user. The capability parameter describes a level of fatigue of the user. It is conceivable that the evaluation unit 16a evaluates a pulse rate and/or a body temperature of the user and determines a capability parameter. The evaluation unit 16a compares data sensed by the sensor unit 36a with read-in and/or stored data, in particular with threshold values. In the present scenario, in the method step 40a, the evaluation unit 16a provides the authorization information at least in dependence on the value of at least one capability parameter of the user.

In one scenario, in at least one method step 42a, the evaluation unit 16a provides the authorization information at least in dependence on at least one item of information relating to at least one spatial working area. The evaluation unit 16a provides the authorization information in dependence on an access authorization of a user to the spatial working area and/or in dependence on a permission to use the at least one object 10a in the spatial working area. The method step 42a forms the evaluation step 102a or the evaluation unit 16a performs the method step 42a as a substep of the evaluation step 102a. It is conceivable that the method step 42a is omitted.

In one scenario, at least in one method step 44a, the evaluation unit 16a actively adapts the authorization information to a changed access authorization of the user to the spatial working area and/or to a changed permission to use the at least one object 10a in the spatial working area. The working step 44a forms an adaptation step 112a or the evaluation unit 16a performs the method step 44a as a substep of the adaptation step 112a. In the scenario, a central authorization point adapts the access authorization of the user and/or the permission to use the at least one object 10a to the spatial working area on the basis of a changed assessment of the potential danger, for example as a result of construction and/or transport work, as a result of exposure to harmful substances, radiation exposure or as a result of emission protection measures. It is conceivable that the access authorization of the user and/or the permission to use the at least one object 10a can be adapted on the basis of further mechanisms that appear appropriate to a person skilled in the art, for example on the basis of simultaneously performed work orders involving a number of objects (10a, 12a, 14a). In the present scenario, the evaluation unit 16a checks regularly, for example every ten minutes, the access authorization of the user and/or the permission to use the at least one object 10a in relation to the spatial working area and provides a possibly changed item of authorization information.

Figure 8:
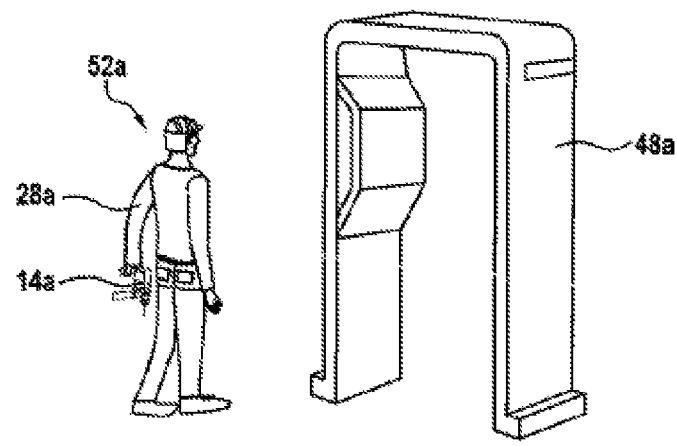
FIG. 8 shows a view of the user with the object and an infrastructure unit.

In one scenario, in at least one method step 46a, the at least one evaluation unit 16a exchanges data with at least one infrastructure unit 48a (cf. FIG. 8). In the present exemplary embodiment, the infrastructure unit 48a is formed as a gate. It is conceivable that the infrastructure unit 48a is formed as an access control, as a passageway, as a door, as an area or a room or as some other unit that appears appropriate to a person skilled in the art. In a data exchange with the evaluation unit 16a, the infrastructure unit 48a transmits at least one identifier for a unique assignment of the infrastructure unit 48a to a spatial working area. The evaluation unit 16a assigns the identifier to an access authorization and/or a permission to use something. It is conceivable that the infrastructure unit 48a directly transmits data on an access authorization for the user and/or a group of users and/or a permission to use the object 10a to the evaluation unit 16a. The method step 46a forms the data exchange step 108a or the data exchange step 108a comprises the method step 46a as a substep.

In one scenario, in at least one method step 50a, the evaluation unit 16a provides the authorization information at least in dependence on at least one item of information on the personal protective equipment 52a. The evaluation unit 16a evaluates the at least one item of information on the personal protective equipment 52a and provides the authorization information on the basis of an evaluation result. In the at least one method step 50a, the evaluation unit 16a provides the authorization information in dependence on a necessity for the personal protective equipment 52a for using the at least one object 10a and/or in dependence on a necessity for the personal protective equipment 52a for the spatial working area. The evaluation unit 16a for example evaluates the authorization data received in the data exchange step 108a described above and/or authorization data stored in the evaluation unit 16a and checks for example whether it contains a necessity for the personal protective equipment 52a for the at least one object 10a and/or for the spatial working area. It is conceivable that the personal protective equipment 52a is required specifically for a certain user, for example if the user suffers from an allergy.

In one scenario, in at least one method step 54a, the evaluation unit 16a actively adapts the authorization information to a changed necessity for the personal protective equipment 52a for the at least one spatial working area. The method step 54a forms the adaptation step 112a or the evaluation unit 16a performs the method step 54a as a substep of the adaptation step 112a. It is conceivable that the method step 54a is omitted. In the scenario, a central authorization point adapts the necessity for the personal protective equipment 52a for the spatial working area on the basis of a changed potentially dangerous situation, for example as a result of construction and/or transport work. It is conceivable that the access authorization of the user and/or the permission to use the at least one object 10a can be adapted on the basis of further mechanisms that appear appropriate to a person skilled in the art, for example on the basis of simultaneously performed work orders involving a number of objects 10a, 12a, 14a. In the present scenario, the evaluation unit 16a checks regularly, for example every ten minutes, the necessity for the personal protective equipment 52a for the spatial working area and possibly provides a changed item of authorization information. It is conceivable that the evaluation unit 16a regularly checks the completeness of the personal protective equipment 52a and possibly provides a changed item of authorization information.

In one scenario, in at least one method step 57a, at least one wear sensor unit 56a of the authorization device 20a senses at least one value for a determination of a state of wear of the personal protective equipment 52a and transmits the value to the evaluation unit 16a. An area sensor of the wear sensor unit 56a that is arranged on a textile of the personal protective equipment 52a senses an integrity of the textile. It is conceivable that the wear sensor unit 56a is intended for accumulating sensor values. The method step 57a forms the data sensing step 110a or the data sensing step 110a comprises the method step 57a as a substep. It is conceivable that the method step 57a is omitted.

The evaluation unit 16a receives data sensed and/or accumulated by the wear sensor unit 56a and evaluates them. The evaluation unit 16a determines and/or assesses a state of wear of the personal protective equipment 52a. For example, the evaluation unit 16a compares the data sensed by the wear sensor unit 56a with data stored in the evaluation unit 16a and/or with data read in, in particular with threshold values. In the present scenario, in at least one method step 120a, the evaluation unit 16a determines the authorization information in dependence on the state of wear of the personal protective equipment 52a. The method step 120a forms the evaluation step 102a or the evaluation unit 16a performs the method step 120a as a substep of the evaluation step 102a.

In one scenario, in at least one method step 60a, at least one scanning unit 58a of the authorization device 20a senses an arrangement of the personal protective equipment 52a. An optical sensor of the scanning unit 58a senses positions of optical markings which are arranged on the personal protective equipment 52a. Alternatively or additionally, an RFID reader senses positions of RFID tags, which are arranged on the personal protective equipment 52a. For sensing the arrangement of the personal protective equipment 52a, the scanning unit 58a is moved past elements of the personal protective equipment 52a, for example by a corresponding scanning movement of the extremity 28a of the user to which the fastening unit 26a is fastened. It is conceivable that at least one scanning unit arranged on the infrastructure unit 48a senses an arrangement and/or a state of use of the personal protective equipment 52a and transmits sensed data to the evaluation unit 16a. The method step 60a forms the data sensing step 110a or the data sensing step 110a comprises the method step 60a as a substep. It is conceivable that the method step 60a is omitted. The scanning unit 58a is connected in signaling terms to the evaluation unit 16a and transmits the positions of the optical markings and/or the RFID tags to the evaluation unit 16a. For example, the personal protective equipment 52a comprises a helmet 114a, boot 116a, goggles 118a and a jacket 122a.

The evaluation unit 16a receives the data transmitted by the scanning unit 58a and evaluates them. The evaluation unit 16a compares the data received from the scanning unit 58a with stored and/or read-in data on a desired arrangement of the personal protective equipment 52a. In the present scenario, in at least one method step 124a, the evaluation unit 16a determines the authorization information in dependence on the arrangement of the personal protective equipment 52a. The method step 124a forms the evaluation step 102a or the evaluation unit 16a performs the method step 124a as a substep of the evaluation step 102a.

Figure 10:
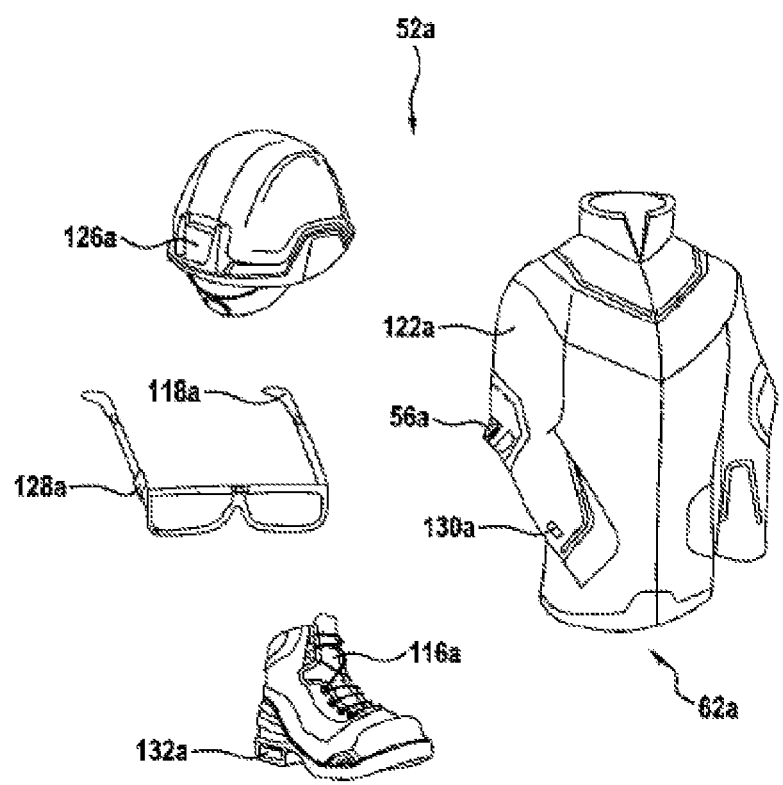
FIG. 10 shows elements of an item of personal protective equipment, with sensors for sensing data for the authorization.

In one scenario, in at least one method step 64a, at least one sensor unit 62a senses a state of use of the personal protective equipment 52a and/or a movement carried out with the personal protective equipment 52a. The sensor unit 62a has a plurality of acceleration sensors 126a, 128a, 130a, 132a, which are arranged on elements of the personal protective equipment 52a. Each time the personal protective equipment 52a is put on, the acceleration sensors 126a, 128a, 130a, 132a sense a movement pattern of the respective element of the personal protective equipment 52a and/or an end position of the respective element at an end of an operation in which the personal protective equipment 52a is put on. Furthermore, in a working operation, the acceleration sensors 126a, 128a, 130a, 132a in each case sense a movement pattern of the respective element of the personal protective equipment 52a. The sensor unit 62a transmits the sensed movement patterns and/or further sensed data to the evaluation unit 16a (cf. FIG. 10). The method step 64a forms the data sensing step 110a or the data sensing step 110a comprises the step 64a as a substep. It is conceivable that the method step 64a is omitted.

The evaluation unit 16a receives the movement patterns transmitted by the sensor unit 62a and evaluates them. In at least one method step 66a, the evaluation unit 16a evaluates the movement carried out with the personal protective equipment 52a. The evaluation unit 16a compares the data received from the sensor unit 62a with stored and/or read-in movement patterns, which are derived from a desired arrangement of the personal protective equipment 52a. The evaluation unit 16a evaluates the movement patterns received from the sensor unit 62a in dependence on a state of the fastening unit 26a. After the closing of the fastening unit 26a, the evaluation unit 16a compares the movement patterns received from the sensor unit 62a with movement patterns that correspond to an operation for putting on the personal protective equipment 52a. The evaluation unit 16a provides the authorization information in dependence on an evaluation result of the movement patterns. In an operation for putting on the personal protective equipment 52a, in which a movement pattern allows the conclusion that the personal protective equipment 52a has been put on incompletely and/or improperly, the evaluation unit 16a disables use of the object 10a. The method step 66a forms the evaluation step 102a or the evaluation unit 16a performs the method step 66a as a substep of the evaluation step 102a.

Figure 11:
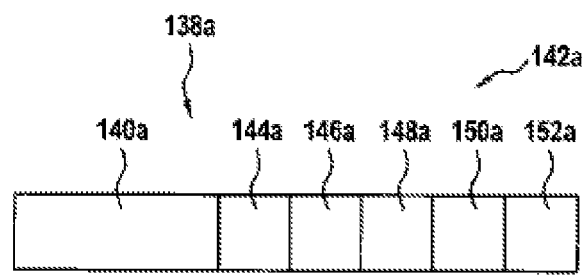
FIG. 11 shows an authorization code of the authorization method.

In at least one method step 68a, the at least one evaluation unit 16a wirelessly exchanges data with the at least one object 10a. The evaluation unit 16a transmits the authorization information wirelessly to the object 10a. The evaluation unit 16a transmits the authorization information to the object 10a by means of a wireless communication interface 134a, which is intended for a data exchange corresponding to a standard for a data transmission, for example corresponding to the Bluetooth standard, corresponding to the Wi-Fi Direct standard and/or corresponding to some other standard that appears suitable to a person skilled in the art. An electronic closing unit 136a of the object 10a enables the object 10a in dependence on the value of the authorization information or disables use of the object 10a. In the present exemplary embodiment, the authorization information is formed as an authorization code 138a, which comprises a daily-updated key 140a and a dynamic key 142a. The daily-updated key 140a contains coded information on the work order. The dynamic key 142a contains values on loading variables, such as an amount of vibration 144a, an amount of noise 146a, a radiation exposure 148a, a stress level 150a and also a working time 152a accumulated over a working day (cf. FIG. 11). It is conceivable that the electronic closing unit 136a has an output element that outputs a closed state recognizably for a user. It is conceivable that, in an optional method step, the object 10a carries out a self-diagnosis and transmits data of the self-diagnosis to the evaluation unit 16a. The evaluation unit 16a evaluates the data of the self-diagnosis, for example the evaluation unit 16a compares data of the self-diagnosis with threshold values and/or desired values. The evaluation unit 16a determines the authorization information in dependence on an evaluation result.

In one scenario, in at least one method step 70a, the evaluation unit 16a wirelessly exchanges data with at least one further object 12a. In the present scenario, the further object 12a is formed as a machine accessory container. It is conceivable that the further object 12a is formed as some other container, for example for keeping other working aids, or as a further machine, for example a further hand-held power tool. The evaluation unit 16a determines an item of authorization information that indicates whether the further object 12a may be used in the use assessed by the authorization device 20a. The authorization information indicates whether the further object 12a may be used by the user in the use assessed by the authorization device 20a. In the present scenario, the evaluation unit 16a determines the authorization information on the use of the object 10a and the authorization information on the use of the further object 12a in mutual dependence. It is conceivable that the evaluation unit 16a determines the authorization information on the use of the object 10a and the authorization information on the use of the further object 12a independently of one another.

In one scenario, in the at least one method step 70a, the evaluation unit 16a wirelessly exchanges data with at least one third object 14a. In the present scenario, the third object 14a is formed as a hand-held power tool. The object 14a is formed as a hammer drill. The evaluation unit 16a determines an item of authorization information that indicates whether the third object 14a may be used in the use assessed by the authorization device 20a. The authorization information indicates whether the third object 14a may be used by the user in the use assessed by the authorization device 20a.

In one scenario, in at least one method step 72a, the at least one evaluation unit 16a exchanges data with at least one authorization database. The evaluation unit 16a reads out the use-related authorization data from the authorization database. For example, the evaluation unit 16a exchanges with the authorization database authorization data relating to the user, relating to the work order, relating to a spatial working area and/or relating to an item of personal protective equipment 52a. For example, the evaluation unit 16a reads out from the authorization database education data of the user, schedules, access authorization data, movement patterns and/or permission to use data. In the present scenario, the evaluation unit 16a exchanges data with the authorization database via a network. The authorization database is formed as an element of a cloud. It is conceivable that the evaluation unit 16a and the authorization database are in each case formed as an element of one and the same local network. It is conceivable that the evaluation unit 16a exchanges authorization data with the authorization database in dependence on a state and/or in dependence on a change in state of the fastening unit 26a. It is conceivable that the evaluation unit 16a reads out the authorization data from the authorization database during putting on, closing, opening and/or taking off of the fastening unit 26a. The method step 72a forms the data exchange step 108a or the data exchange step 108a comprises the method step 72a as a substep. It is conceivable that the method step 72a is omitted. The evaluation unit 16a determines the authorization information in dependence on data that are provided by the authorization database.

In at least one method step 74a, the evaluation unit 16a transmits an item of information, in particular the authorization information, for an output to a user to at least one output unit 76a. In the present exemplary embodiment, the output unit 76a is arranged on the fastening unit 26a. It is conceivable that the output unit 76a is formed separately from the fastening unit 26a and is for example arranged on the object 10a. The output unit 76a outputs the authorization information determined by the evaluation unit 16a to the user. It is conceivable that the output unit 76a outputs to the user further information concerning use, for example information concerning authorization data that prevent enabling of the object 12a for the user. The output device 76a outputs for example an item of output information concerning an access authorization, a permission to use something, required training and/or a state of the personal protective equipment 52a. In the present exemplary embodiment, the display 156a of the output unit 76a presents the output information, for example by means of at least one text output by means of symbols or in some other way that appears suitable to a person skilled in the art.

In the present exemplary embodiment, in at least one method step 158a, the evaluation unit 16a transmits an item of information, in particular the authorization information, for an output to a user to at least one external output unit 160a. In the present exemplary embodiment, the external output unit 160a is formed as a cell phone. The external output unit 160a outputs to the user the authorization information determined by the evaluation unit 16a. It is conceivable that the external output unit 160a outputs to the user further information concerning use, for example information concerning authorization data that prevent enabling of the object 10a for the user. The output unit 160a outputs for example an item of authorization information concerning an access authorization, permission to use something, required training and/or a state of the personal protective equipment 52a.

In one scenario, in at least one method step 78a, the at least one evaluation unit 16a receives input data from at least one input unit 80a. In the case of use, input data are input into the input unit 80a, in particular by the user. The input unit 80a senses input data. The input data define the use and/or use parameters of the use and/or allow an identification of the user. For example, the input data are formed as an identifier. The input unit 80a is connected in signaling terms to the evaluation unit 16a. The evaluation unit 16a evaluates the input data received from the input unit 80a. The evaluation unit 16a determines the authorization information in dependence on the received input data. It is conceivable that the evaluation unit 16a starts an evaluation in dependence on the input data.

Figure 9:
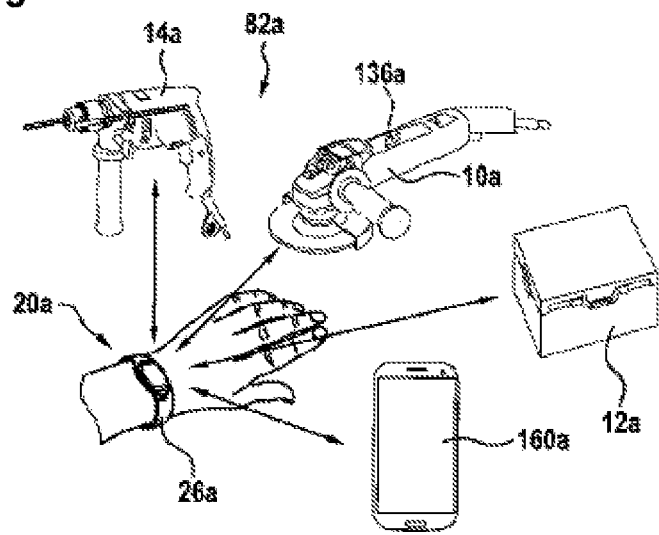
FIG. 9 shows an object system with the authorization device.

FIG. 9 shows an object system 82a with the objects 10a, 12a, 14a and with the electronic authorization device 20a. The electronic authorization device 20a comprises the fastening unit 26a for fastening to an extremity 28a of the user and an evaluation unit 16a.

In the present exemplary embodiment, the fastening unit 26a comprises the arm band 104a. In an open state, the arm band 104a has two open ends. The ends are intended to be connected to one another for putting the arm band 104a on. The fastening unit 26a comprises a closure element 106a, which is intended to connect the open ends of the arm band 104a releasably to one another. The arm band 104a has a hinge 162a. The hinge 162a bears a curved piece 164a of the arm band 104a, which forms one of the open ends.

The fastening unit 26a has a housing 166a. The evaluation unit 16a is arranged in the housing 166a of the fastening unit 26a. The fastening unit 26a is intended to fasten the evaluation unit 16a to an extremity 28a of the user. In the present exemplary embodiment, the evaluation unit 16a comprises a memory element 168a and a processor element 172a. It is conceivable that the evaluation unit 16a has a plurality of memory elements and/or a plurality of processor elements.

The authorization device 20a comprises an energy supply unit 174a. The energy supply unit 174a is arranged in the housing 166a of the fastening unit 26a. In the present exemplary embodiment, the energy supply unit 174a comprises a battery. It is conceivable that, in an alternative exemplary embodiment, the energy supply unit 174a comprises other energy sources, such as for example a solar cell, and additionally or alternatively has further energy stores.

The authorization device 20a comprises the output unit 160a. The output unit 160a is arranged in the housing 166a of the fastening unit 26a. The display 156a of the output unit 160a is arranged on an upper side of the housing 166a. The evaluation unit 16a and the output unit 160a are connected to one another in signaling terms.

Figure 6:
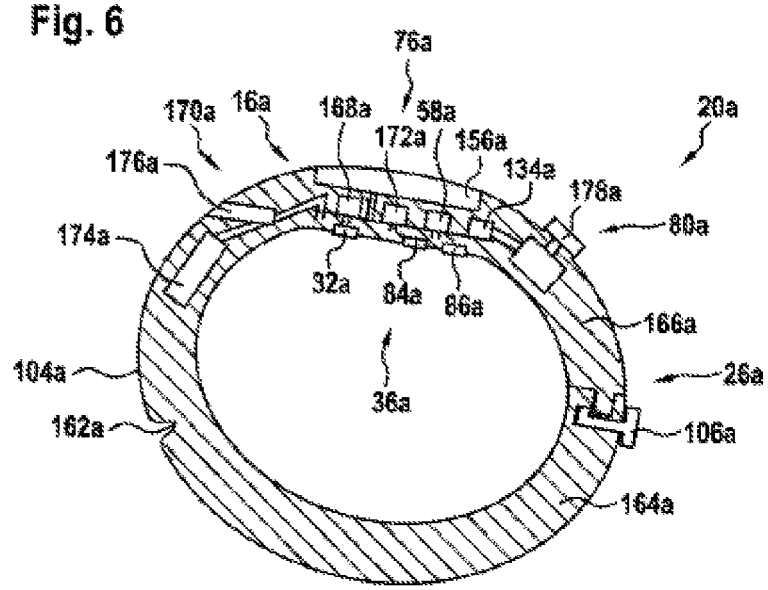
FIG. 6 shows a schematic side view of an authorization device for carrying out the method.

The authorization device 20a comprises the sensor unit 32a for an identification of the user. The sensor unit 32a is connected in signaling terms to the evaluation unit 16a. In the present exemplary embodiment, the sensor unit 32a is fixedly connected to the fastening unit 26a (cf. FIG. 6). The sensor unit 32a is fixedly arranged on the arm band 104a of the fastening unit 26a. The sensor unit 32a has at least one sensor, which in a closed state of the fastening unit 26a is arranged on a side of the arm band 104a that is facing the body of the user. In a closed state and/or in a put-on state of the fastening unit 26a, the sensor is in contact with the skin of the user. It is conceivable that the sensor unit 32a has at least one further sensor on another side of the fastening unit 26a, in particular on an upper side facing away from the user.

The sensor unit 36a is intended for sensing loads acting on the user. The sensor unit 36a is connected in signaling terms to the evaluation unit 16a. In the present exemplary embodiment, the sensor unit 36a is fixedly connected to the fastening unit 26a. The sensor unit 36a is fixedly connected to the arm band 104a of the fastening unit 26a. The sensor unit 36a has at least one vibration sensor 84a, which in at least one operating state senses the vibration transmitted from the object 10a to the user. It is conceivable that the sensor unit 36a alternatively or additionally has further sensors deemed appropriate by a person skilled in the art, for example a microphone, a temperature sensor, an air humidity sensor and/or a radiation sensor.

The sensor unit 36a is intended for sensing the capability of the user. The sensor unit 36a has at least one acceleration sensor 86a, which in at least one operating state senses a movement pattern performed by the user. It is conceivable that the sensor unit 36a alternatively or additionally has further sensors deemed appropriate by a person skilled in the art, for example a pulse sensor and/or a temperature sensor.

The authorization device 20a comprises the scanning unit 58a. The scanning unit 58a is fixedly connected to the fastening unit 26a. The scanning unit 58a is connected in signaling terms to the evaluation unit 16a. In the present exemplary embodiment, the scanning unit 58a is an optical sensor, which is intended for sensing positions of optical markings on the protective equipment 52a. Alternatively or additionally, the scanning unit 58a has an RFID reader, which is intended for sensing RFID tags on the protective equipment 52a. In the present exemplary embodiment, the authorization device 20a comprises RFID tags, which are arranged on elements of the personal protective equipment 52a, such as for example on the helmet 114a, on the boot 116a, on the jacket 122a and/or on the goggles 118a.

The authorization device 20a comprises an electrical interface 170a. The authorization device 20a comprises an electrical terminal element 176a. The electrical terminal element 176a is formed as part of the electrical interface 170a. The terminal element 176a is formed as a socket. The terminal element 176a is intended for establishing a cable-bound power supply connection and/or a cable-bound signaling connection.

In the present exemplary embodiment, the evaluation unit 16a has a plurality of communication interfaces 134a. It is conceivable that the evaluation unit 16a has only one communication interface 134a. A first of the communication interfaces 134a is intended for a data exchange with the objects 10a, 12a, 14a. The first communication interface 134a is formed as a wireless communication interface 134a. The first communication interface 134a is formed as a Bluetooth interface. A further communication interface, not represented any more specifically, is intended for a data exchange with the authorization database. The further communication interface is formed as a network interface and is intended for exchanging data with the authorization database by means of a network. It is conceivable that the further communication interface is alternatively formed as a point-to-point interface. A third communication interface, not represented any more specifically, is intended for a data exchange with the at least one infrastructure unit 48a. A fourth communication interface, not represented any more specifically, is intended for a data exchange with the wear sensor unit 56a of the personal protective equipment 52a.

In the present exemplary embodiment, the input unit 80a is arranged on the housing 166a of the fastening unit 26a. The input unit 80a has an input element 178a, which is formed as a pushbutton. It is conceivable that the input unit 80a has further input elements, such as for example a touchpad and/or a keypad.

In FIGS. 12 to 15, two further exemplary embodiments of the disclosure are shown. The following descriptions and the drawings are restricted substantially to the differences between the exemplary embodiments, it being possible in principle also to refer to the drawings and/or the description of the other exemplary embodiments, in particular of FIGS. 1 to 11, with respect to components with the same designations, in particular with respect to components with the same reference numerals. To distinguish between the exemplary embodiments, the letter a has been added after the reference numerals of the exemplary embodiment in FIGS. 1 to 11. In the exemplary embodiments of FIGS. 12 to 15, the letter a has been substituted by the letters b or c.

Figure 12:
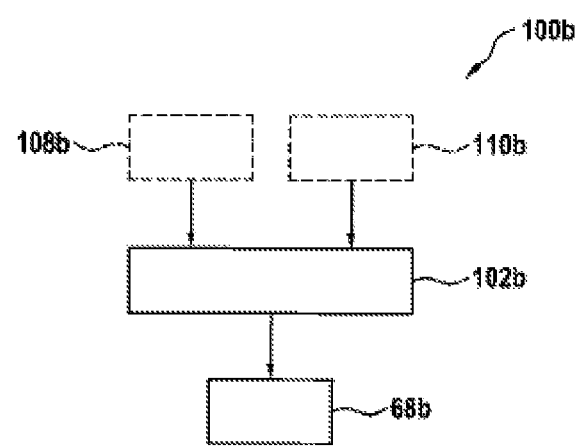
FIG. 12 shows a flow diagram of a method for authorization with at least one external evaluation unit.

FIG. 12 shows a flow diagram 100b of a method for authorizing the use of an object 10b for a further exemplary embodiment. By analogy with the previous exemplary embodiment, the object 10b is formed as a hand-held power tool. In the method, an evaluation unit 16b of an electronic authorization device 20b provides an item of authorization information at least in dependence on at least one item of use-related information. The use-related information relates for example to a work order, to a user, to an item of protective equipment and/or to a working area, such as for example to a building, to an area of a building, to an area or a room and/or to part of a site. The authorization information indicates whether the object 10b may be used for the use assessed by the authorization device 20b. In at least one evaluation step 102b, the authorization unit 16b evaluates at least one item of use-related information and from it determines the authorization information. The authorization information is used for enabling or disabling the object 10b.

By analogy with the previous exemplary embodiment, in a data sensing step 110b, a sensor unit or a plurality of sensor units senses or sense use-related data. The data relate for example to a work order, to a user, to an item of personal protective equipment and/or to a working area. The sensor unit or the sensor units transmit(s) the sensed data to the evaluation unit 16b. It is conceivable that the data sensing step 110b is omitted and the evaluation unit 16b merely processes stored authorization data.

By analogy with the previous exemplary embodiment, in a data exchange step 108b, the evaluation unit 16b reads in authorization data. It is conceivable that, in the data exchange step 108b, the evaluation unit 16b stores authorization data, erases authorization data, for example authorization data of a previous work order, and/or activates or deactivates authorization data, for example authorization data stored in the evaluation unit 16b. The evaluation unit 16b reads in the data from an authorization database and/or from an infrastructure unit. It is conceivable that the data exchange step 108b is omitted.

As a difference from the previous exemplary embodiment, an external evaluation unit 18b evaluates data on providing the authorization information and transmits at least one evaluation result to the at least one evaluation unit 16b. The evaluation units 16b, 18b are connected in signaling terms and transmit authorization data and/or authorization information. It is conceivable that, in a further data exchange step or as an alternative to the data exchange step 108b, the external evaluation unit 18b reads in authorization data from the authorization database, from a further authorization database and/or from an infrastructure unit. It is conceivable that, in a further data sensing step, the external evaluation unit 18b reads out data from the sensor unit and/or from the further sensor unit.

In at least one method step 68b, the at least one evaluation unit 16b wirelessly exchanges data with the at least one object 10b. The evaluation unit 16b transmits the authorization information wirelessly to the object 10b.

Figure 13:
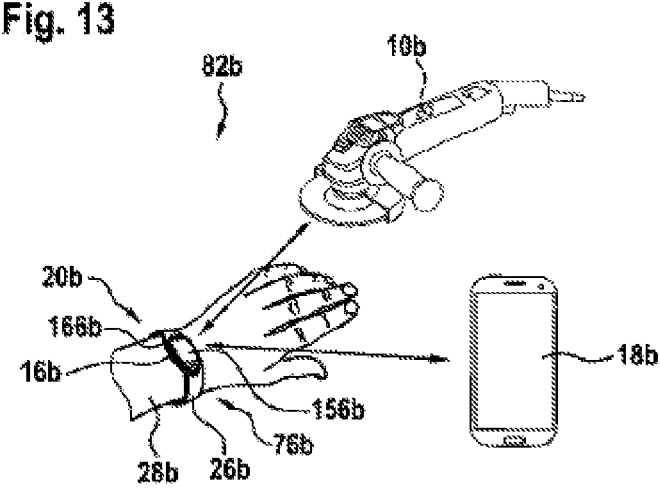
FIG. 13 shows an object system for carrying out the method, with an external evaluation unit.

FIG. 13 shows an object system 82b with the object 10b and with the electronic authorization device 20b. By analogy with the previous exemplary embodiment, the electronic authorization device 20b comprises a fastening unit 26b for fastening to an extremity 28b of the user and also the evaluation unit 16b. As a difference from the previous exemplary embodiment, the authorization device 20b has the further, external evaluation unit 18b.

In the present exemplary embodiment, the external evaluation unit 18b is formed as a smartphone. The external evaluation unit 18b has a memory element not represented any more specifically and a processor element not represented any more specifically. The external evaluation unit 18b is intended for providing an item of authorization information at least in dependence on at least one item of use-related information and transmitting it to the evaluation unit 16b.

By analogy with the previous exemplary embodiment, the authorization unit 20b comprises an output unit 76b. The output unit 76b is arranged in a housing 166b of the fastening unit 26b. The output unit 76b comprises a display 156b. The display 156b is arranged on an upper side of the housing 166b. The evaluation unit 16b and the output unit 76b are connected in signaling terms to one another.

In the present exemplary embodiment, the evaluation unit 16*b* has a plurality of communication interfaces. It is conceivable that the evaluation unit 16*b* and the external evaluation unit 18*b* are at least partially redundantly formed and that the external evaluation unit 18*b* has an interface for a data exchange with the object 10*b*. It is conceivable that, by analogy with the previous exemplary embodiment, the authorization device 20*b* has a sensor unit for identifying the user. It is also conceivable that, by analogy with the previous exemplary embodiment, the authorization device 20*b* has a sensor unit for sensing loads acting on the user and also further sensor units that appear appropriate to a person skilled in the art for determining authorization data.

Figure 14:
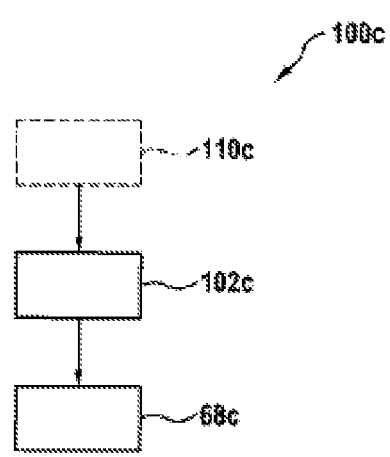
FIG. 14 shows a flow diagram of a method for authorizing use of a vehicle and FIG. 15 shows an authorization device with the vehicle.
Figure 15:
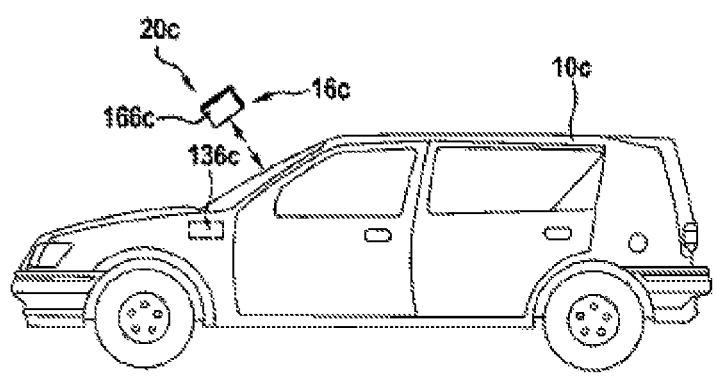

FIG. 14 shows a flow diagram 100*c* of a method for authorizing the use of an object 10*c* for a further exemplary embodiment. In the present exemplary embodiment, the object 10*c* is formed as a motor vehicle. In the method, an evaluation unit 16*c* of an electronic authorization device 20*c* provides an item of authorization information at least in dependence on at least one item of use-related information. In the present exemplary embodiment, the use-related information relates to a work order and/or to a user. The authorization information indicates whether the object 10*c* may be used for the use assessed by the authorization device 20*c*. In at least one evaluation step 102*c*, the evaluation unit 16*c* evaluates at least one item of use-related information and from it determines the authorization information. The authorization information is used for enabling or disabling an object 10*c*. In the present exemplary embodiment, the authorization device 20*c* has a housing 166*c*, in which the evaluation unit 16*c* is arranged. The housing 166*c* is for example formed in the form of a key card or in some other form that appears suitable to a person skilled in the art, for example in the form of a token.

In one scenario, in at least one method step, at least one sensor unit senses data, in particular individual body data, of the user for an identification of the user and transmits the data to the evaluation unit 16*c*. It is also conceivable that the evaluation unit 16*c* identifies the user on the basis of input data, for example a keyword or a code. It is also conceivable that a sensor unit senses an identification document and/or authorization document, for example an identity card and/or a driver's license, whereby the user can be identified, and/or whereby a characteristic of the user, such as for example an age and/or a qualification, can be established. The method step forms a data sensing step 110*c* or the data sensing step 110*c* has the method step as a substep. It is conceivable that this method step is omitted. Alternatively, the evaluation unit 16*c* may be fixedly assigned to the user.

The evaluation unit 16*c* receives data sensed by the sensor unit for sensing user data and evaluates them. The evaluation unit 16*c* identifies the user by means of the data sensed by the sensor unit, for example the evaluation unit 16*c* compares the data sensed by the sensor unit with data stored in the evaluation unit 16*c* and/or with data read in. In the present scenario, in at least one method step, the evaluation unit 16*c* determines the authorization information in dependence on the identification of the user. The evaluation unit 16*c* reads a qualification and/or an age of the user from a memory and determines an item of authorization information at least on the basis of the data read out.

In at least one method step 68*c*, the at least one evaluation unit 16*c* wirelessly exchanges data with the at least one object 10*c*. The evaluation unit 16*c* wirelessly transmits the authorization information to the object 10*c*. In dependence on the value of the authorization information, an electronic closing unit 136*c* of the object 10*c* enables the object 10*c* or disables use of the object 10*c* (cf. FIG. 15). The evaluation unit 16*c* is formed as an electronic key.

In the present exemplary embodiment, the electronic closing unit 136*c* sets use parameters in dependence on an identification of the user and/or in dependence on characteristics of the user, such as for example in dependence on a qualification and/or an age. In the present exemplary embodiment, the closing unit 136*c* sets a maximum output of a drive unit of the motor vehicle and/or a maximum speed of the motor vehicle. The closing unit 136*c* is connected in signaling terms to an open-loop and/or closed-loop control unit of the motor vehicle. It is conceivable that the closing unit 136*c* is integrated in the open-loop and/or closed-loop control unit of the motor vehicle.

What is claimed is:

1. A method for authorizing use of at least one power tool with an electronic authorization device having a sensor unit and an evaluation unit, the method comprising:
   sensing with the sensor unit a body parameter of a user that includes at least one of a blood pressure, a pulse rate, and a body temperature of the user;
   evaluating the sensed body parameter with the evaluation unit;
   determining authorization information based on the evaluated body parameter with the evaluation unit; and
   enabling or disabling operation of the power tool based on the determined authorization information with the electronic authorization device.

2. The method according to claim 1, further comprising:
   determining, with the evaluation unit, the authorization information based further on at least one item of information relating to the user.

3. The method according to claim 1, further comprising:
   fastening the at least one evaluation unit to an extremity of the user using a fastening unit of the electronic authorization device.

4. A method for authorizing use of at least one power tool with an electronic authorization device having a sensor unit and an evaluation unit, the method comprising:
   sensing with the sensor unit a body parameter of a user;
   evaluating the sensed body parameter with the evaluation unit;
   determining authorization information based on the evaluated body parameter with the evaluation unit;
   enabling or disabling operation of the power tool based on the determined authorization information with the electronic authorization device;
   fastening the at least one evaluation unit to an extremity of the user using a fastening unit of the electronic authorization device; and
   determining the authorization information based on a state of the fastening unit and a change in state of the fastening unit,
   wherein the fastening unit is configurable in a closed state in which the evaluation unit is held on to the extremity of the user,
   wherein the fastening unit is configurable in an open state in which the evaluation unit is removable from the extremity of the user,
   wherein the electronic authorization device enables operation of the power tool when the fastening unit is configured in the closed state,
   wherein the change in state of the fastening unit occurs when the fastening unit changes from the closed state to the open state, and wherein the electronic authorization device disables operation of the power tool when the change in state is determined.

5. The method according to claim 2, further comprising:
sensing, with the sensor unit, at least one of (i) at least one loading variable acting on the user, and (ii) a value of a capability parameter of the user; and
transmitting, with the sensor unit, the at least one of (i) the at least one loading variable acting on the user, and (ii) the value of the capability parameter of the user to the evaluation unit.

6. The method according to claim 2, further comprising:
providing, with the at least one evaluation unit, the authorization information at least based on at least one of (i) a level of training of the user, (ii) a value of at least one loading variable acting on the user, and (iii) a value of at least one capability parameter of the user.

7. The method according to claim 1, further comprising:
providing, with the evaluation unit, the authorization information at least based on at least one item of information relating to at least one spatial working area.

8. The method according to claim 7, further comprising:
providing, with the at least one evaluation unit, the authorization information at least based on at least one of (i) an access authorization of the user to the at least one spatial working area, and (ii) a permission to use the at least one object in the at least one spatial working area; and
actively adapting, with the at least one evaluation unit, the authorization information to at least one of (i) a changed access authorization of the user to the at least one spatial working area, and (ii) to a changed permission to use the at least one object in the at least one spatial working area.

9. The method according to claim 1, further comprising:
providing, the at least one evaluation unit, the authorization information at least based on at least one item of information relating to an item of personal protective equipment.

10. The method according to claim 9, further comprising:
providing, the at least one evaluation unit, the authorization information based on at least one of (i) a necessity for the item of personal protective equipment for using the at least one object, and (ii) a necessity for the item of personal protective equipment for at least one spatial working area; and
actively adapting, with the at least one evaluation unit, the authorization information to a changed necessity for the item of personal protective equipment for the at least one spatial working area.

11. The method according to claim 9, further comprising:
sensing, with at least one wear sensor unit of the electronic authorization device, at least one value for determining a state of wear of the item of personal protective equipment; and
transmitting, with the at least one wear sensor unit, the at least one value for determining the state of wear of the item of personal protective equipment to the at least one evaluation unit.

12. The method according to claim 9, further comprising:
sensing, with at least one scanning unit of the electronic authorization device, an arrangement of the item of personal protective equipment.

13. The method according to claim 9, further comprising:
sensing, with at least one sensor unit, at least one of (i) a state of use of the item of personal protective equipment, and (ii) a movement carried out with the item of personal protective equipment; and
transmitting, with the at least one sensor unit, the at least one of (i) the state of use of the item of personal protective equipment, and (ii) the movement carried out with the item of personal protective equipment to the at least one evaluation unit.

14. The method according to claim 13, further comprising:
evaluating, with the at least one evaluation unit, the movement carried out with the item of personal protective equipment.

15. The method according to claim 1, further comprising at least one of:
wirelessly exchanging, with the at least one evaluation unit, data with the at least one object;
wirelessly exchanging, with the at least one evaluation unit, data with at least one further object;
exchanging, with the at least one evaluation unit, data with at least one infrastructure unit;
exchanging, with the at least one evaluation unit, data with at least one authorization database.

16. The method according to claim 1; further comprising:
evaluating, with at least one external evaluation unit, data on providing the authorization information; and
transmitting, with the at least one external evaluation unit, at least one result of the evaluation to the at least one evaluation unit.

17. The method according to claim 1, further comprising at least one of:
transmitting, with the at least one evaluation unit, an item of information for an output to the user to at least one output unit; and
receiving, with the at least one evaluation unit, input data from at least one input unit.

* * * * *